United States Patent
Yang et al.

(10) Patent No.: US 11,747,044 B2
(45) Date of Patent: Sep. 5, 2023

(54) INSTANT WATER BOILING DEVICE

(71) Applicant: GUANGZHOU SEAGULL KITCHEN AND BATH PRODUCTS CO., LTD., Guangzhou (CN)

(72) Inventors: Yuanhung Yang, New Taipei (CN); Andy Ou, Xinyi (CN)

(73) Assignee: GUANGZHOU SEAGULL KITCHEN AND BATH PRODUCTS CO., LTD., Guangzhou (CN)

( * ) Notice: Subject to any disclaimer, the term of this patent is extended or adjusted under 35 U.S.C. 154(b) by 0 days.

(21) Appl. No.: 17/660,139

(22) Filed: Apr. 21, 2022

(65) Prior Publication Data
US 2023/0175731 A1    Jun. 8, 2023

(30) Foreign Application Priority Data

Dec. 8, 2021 (CN) .......................... 202111495474.4
Dec. 8, 2021 (CN) .......................... 202123069356.5

(51) Int. Cl.
*F24H 1/18* (2022.01)
*F24H 15/184* (2022.01)
(Continued)

(52) U.S. Cl.
CPC ............. *F24H 1/18* (2013.01); *F24H 15/184* (2022.01); *F24H 15/219* (2022.01); *G01N 33/1826* (2013.01)

(58) Field of Classification Search
CPC ........ F24H 1/18; F24H 15/184; F24H 15/219; F24H 9/12; F24H 9/13; C02F 2307/06;
(Continued)

(56) References Cited

U.S. PATENT DOCUMENTS 5,511,723 A * 4/1996 Eki ..................... G05D 23/1393
236/12.12
5,816,135 A * 10/1998 Ferri ..................... A47J 31/542
99/290
(Continued)

FOREIGN PATENT DOCUMENTS

DE       102007049550 A1 * 4/2009 ............ F16L 37/088

OTHER PUBLICATIONS

English translation of DE-102007049550-A1, dated Jun. 9, 2023 (Year: 2023).*

*Primary Examiner* — Edelmira Bosques
*Assistant Examiner* — Brett Peterson Mallon
(74) *Attorney, Agent, or Firm* — Platinum Intellectual Property PC (57) ABSTRACT

Provided is an instant water boiling device, which comprises: an instant water boiler provided with a water inlet and a water outlet communicated with a faucet; a control panel arranged on the faucet; and a controller in signal connection with the control panel and the instant water boiler. According to the invention, the control panel is separated from the instant water boiler, which is convenient to install, the instant water boiler with a larger volume can be installed in a cabinet under a tabletop, which saves a space of the tabletop, and meanwhile, the control panel is installed on the faucet, which is convenient for a user to operate the control panel, thus facilitating the operation, simplifying the installation, and saving the space of the tabletop.

8 Claims, 6 Drawing Sheets

(51) Int. Cl.
*F24H 15/219* (2022.01)
*G01N 33/18* (2006.01)

(58) Field of Classification Search
CPC ....... G01N 33/1826; E03C 1/055; E03C 1/05; F16L 37/02; F16L 37/08; F16L 33/035; F16L 37/091
See application file for complete search history.

(56) References Cited

U.S. PATENT DOCUMENTS

| | | | | |
|---|---|---|---|---|
| 5,975,124 | A * | 11/1999 | Stevens, II | E03C 1/05 68/12.22 |
| 6,056,201 | A * | 5/2000 | Ta | G05D 23/1393 236/12.12 |
| 6,753,554 | B1 * | 6/2004 | Gomes | E03C 1/052 257/289 |
| 8,316,883 | B1 * | 11/2012 | Watson | E03C 1/0404 137/551 |
| D814,430 | S * | 4/2018 | Flowers | D13/174 |
| 2007/0152074 | A1 * | 7/2007 | Stowe | E03C 1/055 236/12.1 |
| 2020/0191414 | A1 * | 6/2020 | Peng | F24H 9/2014 |
| 2020/0308036 | A1 * | 10/2020 | Trant | C02F 5/08 |

* cited by examiner

INSTANT WATER BOILING DEVICE

TECHNICAL FIELD

The present invention relates to the technical field of household appliances. More particularly, the present invention relates to an instant water boiling device.

BACKGROUND

A control panel of a present water boiler is generally arranged on a water storage tank, and it is necessary to arrange the water storage tank with a larger volume on a tabletop to operate the control panel conveniently, which occupies a larger space on the tabletop.

In addition, most popular water boilers on the market are pre-heated water boilers currently, which need one water storage tank. Water in the water storage tank is pre-boiled first, and then the hot water in the water storage tank is discharged for use when it is needed. The water storage tank needs to be subjected to heat preservation when the tank is not used at ordinary times, so that the pre-boiled water stored in the water tank needs to be re-boiled after a certain period of time, so as to realize the heat preservation function in this way. That is to say, when the water temperature drops, the water has to be re-boiled. However, such repeated boiling of the water may cause a problem of repeatedly boiled water. Moreover, water scales may also be accumulated in the water storage tank, and more and more water scales may be accumulated after long-term use, which greatly affects the water quality.

SUMMARY

One object of the present invention is to solve at least the above problems and to provide at least advantages that will be described hereinafter.

Another object of the present invention is to provide an instant water boiling device, in which a control panel is separated from an instant water boiler, and the control panel is arranged on a faucet, which is convenient for operating the control panel, and may accommodate the instant water boiler in a cabinet under a tabletop, thus facilitating the accommodation of the water boiler and saving a space of the tabletop.

In order to achieve these objects and other advantages according to the present invention, an instant water boiling device is provided, which comprises:

an instant water boiler provided with a water inlet and a water outlet connected with a faucet;

a control panel arranged on the faucet; and a controller in signal connection with the control panel and the instant water boiler.

Preferably, according to the instant water boiling device, the water inlet of the instant water boiler is communicated with a water purifier through a water manifold.

Preferably, according to the instant water boiling device, the instant water boiler comprises:

a shell having a bottom portion provided with the water inlet and a top portion provided with the water outlet; and an instant heating module arranged in the shell and in signal connection with the controller, wherein a water inlet end of the instant heating module is communicated with the water inlet through a water inlet pipe, and a water outlet end of the instant heating module is communicated with the water outlet through a water outlet pipe; the water inlet pipe is provided with a one-way valve, a temperature sensor is arranged between the water outlet pipe and the water outlet end of the instant heating module, and the water outlet pipe is provided with an electromagnetic valve; and the one-way valve, the electromagnetic valve and the temperature sensor are all in signal connection with the controller.

Preferably, according to the instant water boiling device, the instant water boiler further comprises a TDS water-quality detection sensor arranged on the water inlet pipe and located between the one-way valve and the water inlet end of the instant heating module, and the TDS water-quality detection sensor is used for detecting a TDS index of water entering the water inlet pipe; and the TDS water-quality detection sensor is in signal connection with the controller.

Preferably, according to the instant water boiling device, the controller is connected with a mobile phone terminal.

Preferably, according to the instant water boiling device, the control panel is provided with an on-off key, a child-lock key, an unlock key, a temperature adjustment key, a water volume adjustment key and a display screen which are all in signal connection with the controller.

Preferably, according to the instant water boiling device, the faucet comprises a faucet body, a bent pipe and a water outlet nozzle, an upper end of the faucet body is communicated with the water outlet, a lower end of the faucet body is communicated with one end of the bent pipe, and the water outlet nozzle is provided with the other end of the bent pipe.

Preferably, according to the instant water boiling device, the control panel is connected with the faucet body through an installation mechanism, and the installation mechanism comprises:

a first sleeve rotatably sheathed on the faucet tube body, wherein a circumferential edge of a bottom portion of the first sleeve is annularly provided with first sawteeth; and a lower portion of a circumferential side face of the first sleeve is provided with a plurality of poke rods arranged at intervals along a circumferential direction;

a buffer ring slidably arranged on the faucet body along a vertical direction and located below the first sleeve, wherein a circumferential edge of a top portion of the buffer ring is annularly provided with second sawteeth matched with the first sawteeth;

a first spring sheathed on the faucet body and located below the buffer ring, wherein an upper end of the first spring is connected with a bottom portion of the buffer ring, and a lower end of the first spring is connected with the faucet body; and a second sleeve slidably sheathed on the first sleeve along a vertical direction, wherein one side of the control panel is fixedly connected with the second sleeve.

Preferably, according to the instant water boiling device, the circumferential side face of the first sleeve is provided with a first groove along an axial direction of the first sleeve, and the first groove is internally provided with third sawteeth extending along the axial direction of the first sleeve;

a side face of the other side of the control panel is provided with a second groove; and a bottom face of the control panel is provided with an opening; and the installation mechanism further comprises:

an elastic pin slidably arranged in the second groove along a horizontal direction, wherein one end of the elastic pin protrudes from the second groove, and the other end of the elastic pin horizontally extends towards a direction close to the faucet body; and the other end of the elastic pin is connected with the second groove through a second spring arranged horizontally;

a slider having a top portion located in the control panel, a bottom portion located outside the control panel, and a middle portion which is a narrowed portion and slidably arranged in the opening;

a fixing plate fixedly arranged on the bottom face of the control panel and located on one side of the slider far away from the faucet body, wherein the bottom portion of the slider is connected with the fixing plate through a third spring arranged horizontally;

a fixed pulley located in the control panel and located between the slider and the elastic pin;

a rope having one end connected with the other end of the elastic pin and the other end horizontally extending towards a direction close to the faucet body, passing through the fixed pulley, and then connected with the top portion of the slider; and a tooth block capable of being clamped between two adjacent teeth of the third sawteeth, wherein the tooth block is connected with the bottom portion of the slider through a connecting rod, and the connecting rod is slidably connected with the bottom face of the control panel.

Preferably, according to the instant water boiling device, a top portion of a tooth of the first sawteeth and a top portion of a tooth of the second sawteeth both have an arc structure; a joint between two adjacent teeth of the second sawteeth is designed into a rounded corner; and two sides of the teeth of the first sawteeth are both embedded with a plurality of balls in a rolling way.

The present invention at least comprises the following beneficial effects.

1. According to the present invention, the control panel is separated from the instant water boiler, which is convenient to install. The instant water boiler with a larger volume may be installed in a cabinet under a tabletop, which saves a space of the tabletop, and meanwhile, the control panel is installed on the faucet, which is convenient for a user to operate the control panel, thus simplifying the installation and saving the space of the tabletop while facilitating the operation. According to the present invention, the instant water boiler is used, so that the water is used immediately after being boiled without needing to arrange a water storage tank and no repeatedly boiled water will be generated, thus ensuring the quality and the safety of drinking hot water.

2. According to the present invention, the TDS water-quality detection sensor is arranged between the water purifier and the instant water boiler; the quality of the water entering the shell is detected through the TDS water-quality detection sensor, and the quality of water to be heated is monitored in real time. When the TDS index of the water quality exceeds standards, an administrator can replace a filter element of the water purifier as soon as possible according to the detection results, so as to ensure the hygiene and safety of the water used by a user. Further, the controller transmits the received TDS index of the water quality to the mobile phone terminal through wireless signal connection between the controller and the mobile phone terminal, and whether the quality of water purified by the water purifier meets standards may be judged by checking the TDS index on the mobile phone terminal, so as to remind the administrator to replace the filter element of the water purifier.

Other advantages, objects and features of the present invention will be partially reflected by the following description, and will be partially understood by those skilled in the art through study and practice of the present invention.

Description of reference numerals: 100 refers to faucet body; 101 refers to water outlet nozzle; 105 refers to bent pipe; 102 refers to water outlet pipe; 200 refers to control panel; 2001 refers to first groove; 201 refers to on-off key; 202 refers to temperature adjustment key; 203 refers to display screen; 204 refers to water volume adjustment key; 205 refers to unlock key; 300 refers to instant water boiler; 302 refers to water manifold; 303 refers to water purifier; 304 refers to instant heating module; 305 refers to one-way valve; 306 refers to temperature sensor; 307 refers to electromagnetic valve; 308 refers to water inlet; 309 refers to water outlet; 310 refers to TDS water-quality detection sensor; 311 refers to controller; 312 refers to power line; 313 refers to shell; 401 refers to first sleeve; 4011 refers to first sawteeth; 4012 refers to ball; 4013 refers to third sawteeth; 402 refers to poke rod; 403 refers to buffer ring; 4031 refers to second sawteeth; 404 refers to first spring; 405 refers to second sleeve; 501 refers to elastic pin; 502 refers to second spring; 503 refers to slider; 504 refers to fixing plate; 505 refers to third spring; 506 refers to fixed pulley; 507 refers to rope; 508 refers to tooth block; and 509 refers to connecting rod.

DETAILED DESCRIPTION

The present invention is further described in detail hereinafter with reference to the embodiments, so that those skilled in the art can implement according to the text of the specification.

It should be understood that the terms such as "having," "including," and "comprising" as used herein do not exclude the presence or addition of one or more other elements or combinations thereof.

It should be noted that the experimental methods described in the following embodiments are all conventional methods unless otherwise specified. All the reagents and materials can be obtained commercially unless otherwise specified.

In the description of the present invention, the orientations or positional relationships indicated by the terms such as "transverse", "longitudinal", "upper", "lower", "front", "rear", "left", "right", "vertical", "horizontal", "top", "bottom", "inner", "outer" and the like, refer to the orientations or positional relationships shown in the drawings, which are only intended to facilitate describing the present invention and simplifying the description, and do not indicate or imply that the indicated devices or elements must have a specific orientation, be constructed and operated in a specific orientation, and therefore cannot be understood as a limitation of the present invention.

Figure 1:
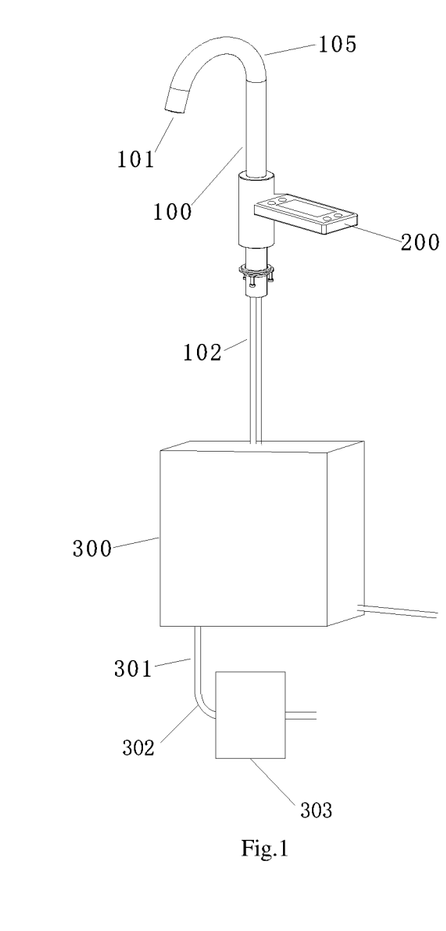
FIG. 1 is a schematic structural diagram of an instant water boiling device according to the present invention.
Figure 2:
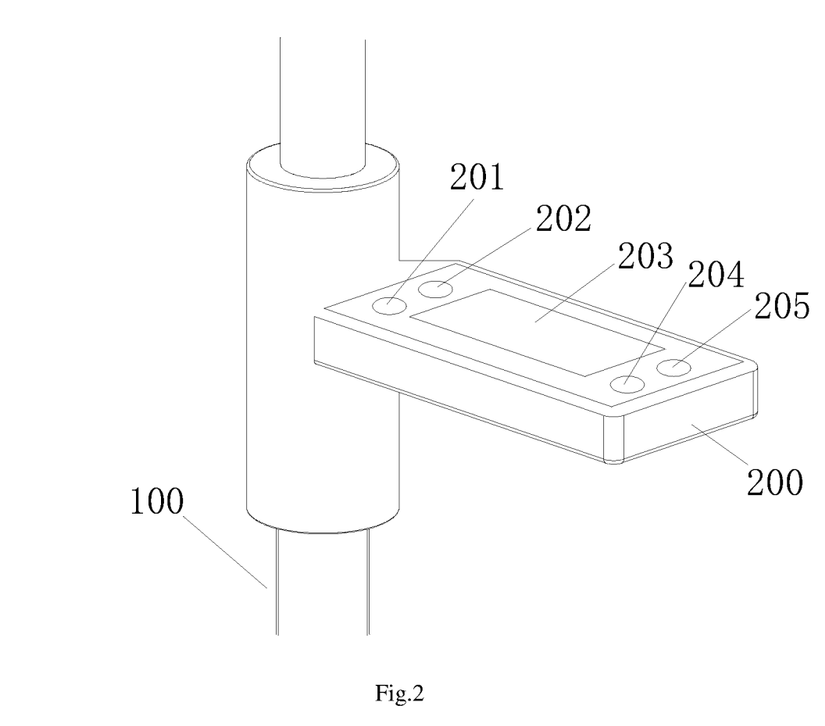
FIG. 2 is a schematic structural diagram of a control panel according to the present invention.

As shown in FIG. 1 to FIG. 2, the present invention provides an instant water boiling device, which comprises:

an instant water boiler 300 provided with a water inlet 308 and a water outlet 309 connected with a faucet;

a control panel 200 arranged on the faucet; and a controller 311 in signal connection with the control panel 200 and the instant water boiler 300.

In the technical solution above, according to the present invention, the control panel 200 is separated from the instant water boiler 300, which is convenient to install, the instant water boiler 300 with a larger volume can be installed in a cabinet under a tabletop, which saves a space of the tabletop, and meanwhile, the control panel 200 is installed on the faucet, which is convenient for a user to operate the control panel 200, thus simplifying the installation and saving the space of the tabletop while facilitating the operation. According to the present invention, the instant water boiler is used, so that the water is used immediately after being boiled without generating repeatedly boiled water and needing not to arrange a water storage tank, thus ensuring the quality and safety of drinking not water.

In another technical solution, according to the instant water boiling device, the water inlet of the instant water boiler 300 is communicated with a water purifier 303 through a water manifold 302.

In the technical solution above, water entering the instant water boiler 300 may be purified and filtered by connecting the water purifier, thus ensuring safety and hygiene of water used.

Figure 6:
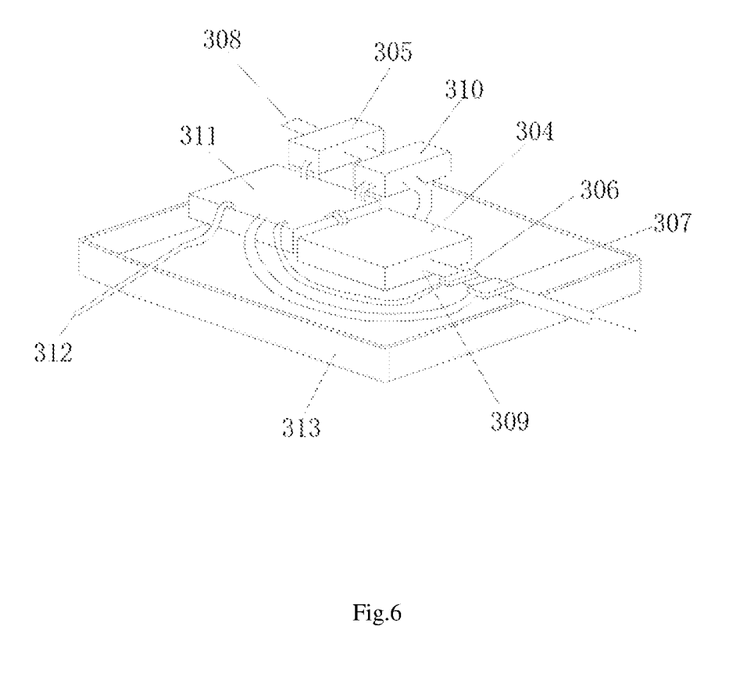
FIG. 6 is a schematic structural diagram of an instant water boiler according to the present invention.

In another technical solution, according to the instant water boiling device, the instant water boiler 300 comprises:
a shell 313 having a bottom portion provided with the water inlet and a top portion provided with the water outlet; and
an instant heating module 304 arranged in the shell and in signal connection with the controller, wherein a water inlet end of the instant heating module is communicated with the water inlet through a water inlet pipe, and a water outlet end of the instant heating module is communicated with the water outlet through a water outlet pipe 102; the water inlet pipe is provided with a one-way valve 305, a temperature sensor 306 is arranged between the water outlet pipe 102 and the water outlet end of the instant heating module, and the water outlet pipe 102 is provided with an electromagnetic valve 307, which is located between the temperature sensor and the water outlet pipe 102; and the one-way valve, the electromagnetic valve and the temperature sensor are all in signal connection with the controller.

In the technical solution above, according to the present invention, the water in need is heated instantly through the instant heating module without needing to preheat the water in advance, thus avoiding "repeatedly boiled water". After receiving an instruction from the control panel 200, the controller controls opening and closing of the one-way valve, and the controller controls opening and closing of the electromagnetic valve according to received water temperature detected by the temperature sensor.

In another technical solution, according to the instant water boiling device, the instant water boiler 300 further comprises a TDS water-quality detection sensor 310 arranged on the water inlet pipe and located between the one-way valve and the water inlet end of the instant heating module, and the TDS water-quality detection sensor is used for detecting a TDS index (a concentration of total dissolved substances in water) of water entering the water inlet pipe. The TDS water-quality detection sensor is in signal connection with the controller. The quality of water entering the shell may be detected through the TDS water-quality detection sensor, and the quality of water to be heated is monitored in real time. When the TDS index of the water quality exceeds standards, an administrator can replace a filter element of the water purifier as soon as possible according to the detection results, so as to ensure the hygiene and safety of water used by the user.

In another technical solution, according to the instant water boiling device, the controller is connected with a mobile phone terminal. The controller transmits the received TDS index of the water quality to the mobile phone terminal, and whether the quality of water purified by the water purifier meets standards currently may be judged by checking the TDS index on the mobile phone terminal, so as to remind the administrator to replace the filter element of the water purifier.

In another technical solution, according to the instant water boiling device, the control panel 200 is provided with an on-off key, a child-lock key, an unlock key 205, a temperature adjustment key 202, a water volume adjustment key 204 and a display screen 203 which are all in signal connection with the controller.

In the technical solution above, the on-off key is used for touch control and transmission of a signal to the controller, and after receiving a touch signal of the on-off key, the controller controls opening of the one-way valve, and water in the water purifier enters the shell. The instant heating module heats the water, and the temperature sensor detects a temperature of the heated water in real time, and transmits a detected temperature signal to the controller. The controller judges whether the electromagnetic valve is opened or not according to a temperature signal value, and when the temperature signal value reaches the water temperature in need, the controller controls opening of the electromagnetic valve, and the water in the shell enters the faucet through the water outlet.

The child-lock key is used for touch control and transmission of a lock signal to the controller, and after receiving the lock signal, the controller stops executing touch signals of the on-off key 201, the temperature adjustment key 202 and the water volume adjustment key. The unlock key 205 is used for touch control and transmission of an unlock signal to the controller, and after receiving the unlock signal, the controller recovers the execution of the touch signals of the on-off key 201, the temperature adjustment key 202 and the water volume adjustment key.

The temperature adjustment key 202 is used for touch control and transmission of a signal to the controller, and after receiving the touch signal of the temperature adjustment key 202, the controller controls a heating power of the instant heating module, so as to control and adjust a water heating temperature.

The water volume adjustment key is used for touch control and transmission of a signal to the controller to adjust opening degrees of the one-way valve and the electromagnetic valve.

The controller transmits a water temperature signal value, a water volume adjustment value and a water temperature adjustment value of the heated water to the display screen 203, which are displayed in real time through the display screen 203. Meanwhile, the controller controls the display screen 203 to display a child-lock symbol or an unlock symbol, and an on/off status symbol of the on-off key. The controller transmits the received TDS index of the water quality to the display screen 203, and the water quality is displayed on the display screen 203 in real time.

In another technical solution, according to the instant water boiling device, the faucet comprises a faucet body 100, a bent pipe 105 and a water outlet nozzle 101, an upper end of the faucet body 100 is communicated with the water outlet, a lower end of the faucet body is communicated with one end of the bent pipe 105, and the water outlet nozzle 101 is provided with the other end of the bent pipe 105. The water outlet of the instant heating module is communicated with the water outlet nozzle 101 through the faucet body 100 and the bent pipe 105, so that hot water heated by the instant heating module is led out, and the bent pipe 105 is designed to enable vertically and upwardly flowing hot water flow to flow downwardly, thus being convenient for the user to take water.

Figure 3:
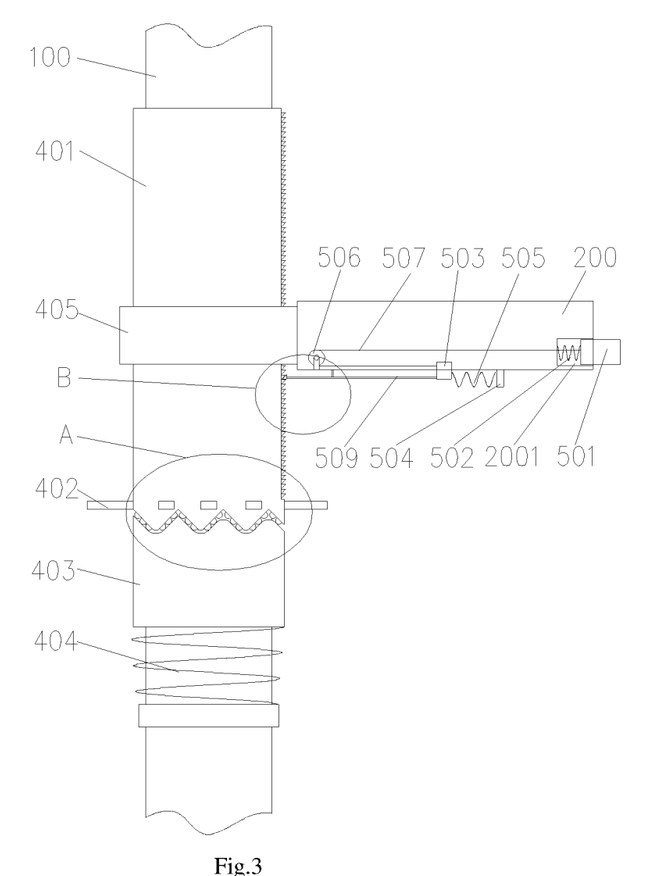
FIG. 3 is a schematic structural diagram of an installation mechanism according to the present invention.
Figure 4:
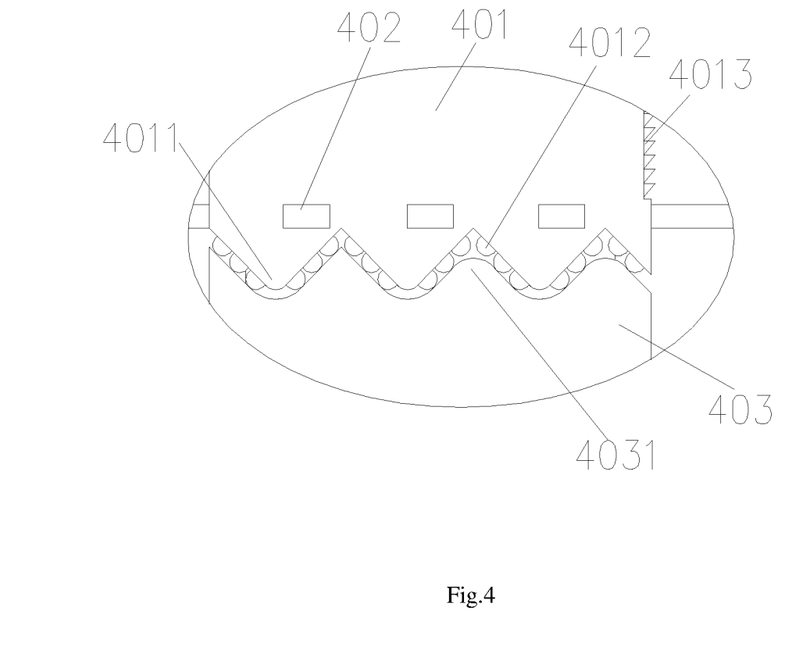
FIG. 4 is a partial enlarged drawing of A in FIG. 3.
Figure 5:
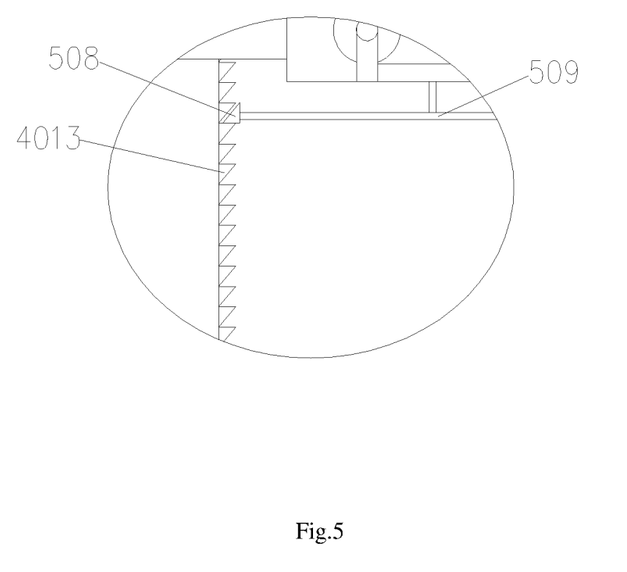
FIG. 5 is a partial enlarged drawing of B in FIGS. 3.

In another technical solution, according to the instant water boiling device, the control panel 200 is connected with the faucet body 100 through an installation mechanism, and as shown in FIG. 3 to FIG. 5, the installation mechanism comprises:

a first sleeve 401 rotatably sheathed on the faucet tube body 100, wherein a circumferential edge of a bottom portion of the first sleeve 401 is annularly provided with first sawteeth 4011; and a lower portion of a circumferential side face of the first sleeve 401 is provided with a plurality of poke rods 402 arranged at intervals along a circumferential direction;

a buffer ring 403 slidably arranged on the faucet body 100 along a vertical direction and located below the first sleeve 401, wherein a circumferential edge of a top portion of the buffer ring is annularly provided with second sawteeth 4031 matched with the first sawteeth 4011; a circumferential face of the faucet body 100 is provided with a first sliding groove along a vertical direction, which is located below the first sleeve 401, and an inner wall of the buffer ring is provided with a first slider 503 slidably arranged in the first sliding groove, so that the buffer ring is slidably connected with the faucet body 100;

a first spring 404 sheathed on the faucet body 100 and located below the buffer ring, wherein an upper end of the first spring 404 is connected with a bottom portion of the buffer ring, and a lower end of the first spring is connected with the faucet body 100; and a second sleeve 405 slidably sheathed on the first sleeve 401 along a vertical direction, wherein one side of the control panel 200 is fixedly connected with the second sleeve 405. The first sleeve 401 is provided with a second sliding groove along a vertical direction, and an inner wall of the second sleeve 405 is provided with a second slider 503 slidably arranged in the second sliding groove, so that the second sleeve 405 is slidably connected with the first sleeve 401.

In the technical solution above, according to the present invention, the control panel 200 is rotatably installed on the faucet body through the installation mechanism, so that a circumferential position of the control panel 200 may be adjusted as required, and a vertical position of the control panel 200 may also be adjusted at the same time, thus being convenient for the user to operate the control panel 200, and improving use comfort.

The first sleeve 401 is rotatably connected with the faucet body 100 through a bearing, and the first sleeve 401 may rotate along a circumferential direction relative to the faucet body 100, thus driving the second sleeve 405 to rotate along a circumferential direction. The second sleeve 405 is slidably arranged on the first sleeve 401 along a vertical direction, and the second sleeve 405 may move along a vertical direction relative to the first sleeve 401, so that the circumferential position and the vertical position of the control panel 200 can be adjusted relative to the faucet body 100 finally, thus being convenient for the user to operate the control panel 200.

According to the present invention, the buffer ring matched with the first sleeve 401 is arranged to buffer circumferential rotation of the first sleeve 401, so as to avoid excessive circumferential rotation of the control panel 200 caused by excessively flexible rotation of the first sleeve 401, or unnecessary rotation of the control panel 200 caused by external touch in a restricted state. When the control panel 200 needs to be rotated, the user applies a rotating force to one adjacent poke rod 402. Under the limiting effect of the buffer ring, the first sleeve 401 can be rotated relative to the faucet body 100 only when the rotating force applied to the poke rod 402 reaches certain strength. The buffer ring is arranged at the bottom portion of the first sleeve 401 in a floating way through the first spring 404. When the first sleeve 401 rotates along a circumferential direction under the action of the rotating force, the first sawteeth 4011 of the first sleeve 401 exert a certain downward pressure on the second sawteeth 4031 of the buffer ring, and any tooth of the first sawteeth 4011 moves along an annular wavy track formed by the teeth of the second sawteeth 4031, so that the buffer ring can limit a speed of rotation of the first sleeve 401, and meanwhile, a situation that the first sleeve 401 cannot rotate due to jamming may not occur.

In another technical solution, according to the instant water boiling device, the circumferential side face of the first sleeve 401 is provided with a first groove 2001 along an axial direction of the first sleeve, and the first groove is internally provided with third sawteeth 4013 extending along the axial direction of the first sleeve 401. The first groove 2001 is located close to one side of the control panel 200, and the first groove 2001 and the second sliding groove do not interfere with each other.

A side face of the other side of the control panel 200 is provided with a second groove; and a bottom face of the control panel 200 is provided with an opening.

The installation mechanism further comprises:

an elastic pin 501 slidably arranged in the second groove along a horizontal direction, wherein one end of the elastic pin 501 protrudes from the second groove, and the other end of the elastic pin horizontally extends towards a direction close to the faucet body 100; and the other end of the elastic pin 501 is connected with the second groove through a second spring 502 arranged horizontally;

a slider 503 having a top portion located in the control panel 200, a bottom portion located outside the control panel 200, and a middle portion which is a narrowed portion and slidably arranged in the opening, wherein the slider 503 has a structure with two large ends (an upper end and a lower end) and a small middle portion, sizes of the top portion and the bottom portion of the slider 503 are both larger than that of the opening, so that the slider 503 is slidably connected with the bottom face of the control panel 200, and the top portion is located inside the control panel 200 and the bottom portion is located outside the control panel 200;

a fixing plate 504 fixedly arranged on the bottom face of the control panel 200 and located on one side of the slider 503 far away from the faucet body 100, wherein the bottom portion of the slider 503 is connected with the fixing plate 504 through a third spring 503 arranged horizontally;

a fixed pulley 506 located in the control panel 200 and located between the slider 503 and the elastic pin 501;

a rope 507 having one end connected with the other end of the elastic pin 501 and the other end horizontally extending towards a direction close to the faucet body 100, passing through the fixed pulley 506, and then connected with the top portion of the slider 503; and a tooth block 508 capable of being clamped between two adjacent teeth of the third sawteeth 4013, wherein the tooth block 508 is connected with the bottom portion of the slider 503 through a connecting rod 509, and the connecting rod 509 is slidably connected with the bottom face of the control panel 200.

In the technical solution above, according to the present invention, the vertical position of the control panel 200 is limited by matching the tooth block 508 with the third sawteeth 4013, and under mutual matching among the elastic pin 501, the second spring 502, the fixed pulley 506, the slider 503, the third spring 505 and the rope 507, the control panel 200 may move downwardly relative to the faucet body by pressing the elastic pin 501, so that the vertical position of the control panel 200 may be adjusted and positioned.

The second spring 502 is a compression spring, the third spring 505 is an extension spring, the tooth block 508 is clamped between two adjacent teeth of the third sawteeth, a vertical section of the tooth block 508 is a right triangle, a vertical section of any tooth of the third sawteeth 4013 is also a right triangle, and a bevel edge of the tooth block 508 is arranged opposite to a bevel edge of the tooth of the third sawteeth 4013, so that the control panel 200 is forcibly pushed upwardly, and an inclined plane of the tooth block 508 may move upwardly along an inclined plane of the tooth of the third sawteeth 4013. When the control panel 200 needs to move downwardly, one end of the elastic pin 501 is pressed manually, and the elastic pin 501 moves towards the faucet body 100 in the second groove. The second spring 502 is further compressed, one end of the rope 507 is loosened, the slider 503 moves far away from the faucet body 100 under an elasticity of the third spring 505, and the tooth block 508 is moved far away from the faucet body 100 through the connecting rod 509. When the elastic pin 501 is pressed to a limiting position, the tooth block 508 and the teeth of the third sawteeth 4013 do not interfere with each other. At the moment, the control panel 200 may be moved vertically and downwardly relative to the faucet body 100, and the control panel 200 is moved vertically and downwardly when the elastic pin 501 is always maintained in a pressed state, until the control panel 200 moves to a required position. A pressing force applied to the elastic pin 501 is released, and under an elasticity of the second spring 502, one end of the rope 507 is moved far away from the faucet body 100. The slider 503 is driven by the rope 507 to move close to the faucet body 100 by turning the fixed pulley 506, so that the tooth block 508 moves close to the faucet body 100, and the tooth block 508 returns to a position between two adjacent teeth of the third sawteeth 4013, thus limiting the vertical position of the control panel 200.

In another technical solution, according to the instant water boiling device, a top portion of a tooth of the first sawteeth 4011 and a top portion of a tooth of the second sawteeth 4031 both have an arc structure; a joint between two adjacent teeth of the second sawteeth 4031 is designed into a rounded corner; and two sides of the teeth of the first sawteeth 4011 are both embedded with a plurality of balls 4012 in a rolling way 4012. The top portion of the tooth of the first sawteeth 4011 and the top portion of the tooth of the second sawteeth 4031 are set into the arc structure, and the joint between two adjacent teeth of the second sawteeth 4031 is processed into the rounded corner. Meanwhile, the balls 4012 are arranged on two sides of the teeth of the first sawteeth 4011, and any ball 4012 is contacted with side portions of the teeth of the second sawteeth 4031, thus improving the smoothness of rotation of the first sleeve 401 relative to the buffer ring, and avoiding the teeth of the first sawteeth 4011 from being jammed between two adjacent teeth of the second sawteeth 4031 to cause the first sleeve 401 to be unable to rotate relative to the buffer ring. The smoothness of rotation of the first sleeve 401 is ensured while ensuring that the rotating flexibility of the first sleeve 401 along the circumferential rotation can be improved to some extent through the buffer ring. In practical application, a height of the teeth of the first sawteeth 4011 and a height of the teeth of the second sawteeth 4031 are controlled to ensure that the user pulls the poke rod 402 manually, and a certain rotating force is applied to the first sleeve 401, so that the first sleeve 401 may rotate around a self-axis relative to the buffer ring, thus adjusting a position of the control panel 200, and being convenient to operate the control panel 200 when the user stands at different positions.

The number and the processing scale of devices described herein are used to simplify the description of the present invention. The application, modification and variation of the present invention are obvious to those skilled in the art.

Although the embodiments of the present invention have been disclosed above, the present invention is not limited to the applications listed in the specification and the implementations. The present invention can be applied to various fields suitable for the present invention absolutely, and other modifications can be easily realized by those skilled in the art. Therefore, the present invention is not limited to the specific details and the illustrations shown and described herein without departing from the general concepts defined by the claims and equivalent scopes.

The invention claimed is:

1. An instant water boiling device, comprising:
   an instant water boiler provided with a water inlet and a water outlet connected with a faucet;
   a control panel arranged on the faucet;
   a controller in signal connection with the control panel and the instant water boiler;
   wherein the faucet comprises a faucet body, a bent pipe and a water outlet nozzle, an upper end of the faucet body is communicated with the bent pipe and a lower end is communicated with the water outlet pipe, and the water outlet nozzle is communicated with the bent pipe;
   wherein the control panel is connected with the faucet body through an installation mechanism, and the installation mechanism comprises:
   a first sleeve rotatably sheathed on the faucet body, wherein a circumferential edge of a bottom portion of the first sleeve is annularly provided with first sawteeth; and a lower portion of a circumferential side face of the first sleeve is provided with a plurality of poke rods arranged at intervals along a circumferential direction;
   a buffer ring slidably arranged on the faucet body along a vertical direction and located below the first sleeve, wherein a circumferential edge of a top portion of the buffer ring is annularly provided with second sawteeth matched with the first sawteeth;
   a first spring sheathed on the faucet body and located below the buffer ring, wherein an upper end of the first spring is connected with a bottom portion of the buffer ring, and a lower end of the first spring is connected with the faucet body; and
   a second sleeve slidably sheathed on the first sleeve along a vertical direction, wherein one side of the control panel is fixedly connected with the second sleeve.

2. The instant water boiling device according to claim 1, wherein the water inlet of the instant water boiler is communicated with a water purifier through a water manifold.

3. The instant water boiling device according to claim 2, wherein the instant water boiler comprises:
   a shell having a bottom portion provided with the water inlet and a top portion provided with the water outlet; and an instant heating module arranged in the shell and in signal connection with the controller, wherein a water inlet end of the instant heating module is communicated with the water inlet through a water inlet pipe, and a water outlet end of the instant heating module is communicated with the water outlet through a water outlet pipe; the water inlet pipe is provided with a one-way valve, a temperature sensor is arranged between the water outlet pipe and the water outlet end of the instant heating module, and the water outlet pipe is provided with an electromagnetic valve; and the one-way valve, the electromagnetic valve and the temperature sensor are all in signal connection with the controller.

4. The instant water boiling device according to claim 3, wherein the instant water boiler further comprises a TDS water-quality detection sensor arranged on the water inlet pipe and located between the one-way valve and the water inlet end of the instant heating module, and the TDS water-quality detection sensor is used for detecting a TDS index of water entering the water inlet pipe; and the TDS water-quality detection sensor is in signal connection with the controller.

5. The instant water boiling device according to claim 4, wherein the controller is connected with a mobile phone terminal.

6. The instant water boiling device according to claim 1, wherein the control panel is provided with an on-off key, a child-lock key, an unlock key, a temperature adjustment key, a water volume adjustment key and a display screen which are all in signal connection with the controller.

7. The instant water boiling device according to claim 1, wherein the circumferential side face of the first sleeve is provided with a first groove along an axial direction of the first sleeve, and the first groove is internally provided with third sawteeth extending along the axial direction of the first sleeve;
  a side face of the other side of the control panel is provided with a second groove; and a bottom face of the control panel is provided with an opening;

the installation mechanism further comprises:
an elastic pin slidably arranged in the second groove along a horizontal direction, wherein one end of the elastic pin protrudes from the second groove, and the other end of the elastic pin horizontally extends towards a direction close to the faucet body; and the other end of the elastic pin is connected with the second groove through a second spring arranged horizontally;
a slider having a top portion located in the control panel, a bottom portion located outside the control panel, and a middle portion which is a narrowed portion and slidably arranged in the opening;
a fixing plate fixedly arranged on the bottom face of the control panel and located on one side of the slider far away from the faucet body, wherein the bottom portion of the slider is connected with the fixing plate through a third spring arranged horizontally;
a fixed pulley located in the control panel and located between the slider and the elastic pin;
a rope having one end connected with the other end of the elastic pin and the other end horizontally extending towards a direction close to the faucet body, passing through the fixed pulley, and then connected with the top portion of the slider; and
a tooth block capable of being clamped between two adjacent teeth of the third sawteeth, wherein the tooth block is connected with the bottom portion of the slider through a connecting rod, and the connecting rod is slidably connected with the bottom face of the control panel.

8. The instant water boiling device according to claim 1, wherein a top portion of a tooth of the first sawteeth and a top portion of a tooth of the second sawteeth both have an arc structure; a joint between two adjacent teeth of the second sawteeth is designed into a rounded corner; and two sides of the teeth of the first sawteeth are both embedded with a plurality of balls in a rolling way.

* * * * *